US006613082B2

(12) United States Patent
Yang

(10) Patent No.: US 6,613,082 B2
(45) Date of Patent: *Sep. 2, 2003

(54) STENT HAVING COVER WITH DRUG DELIVERY CAPABILITY

(76) Inventor: Jun Yang, 46 Foxtail La., Dove Canyon, CA (US) 92679

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/524,244

(22) Filed: Mar. 13, 2000

(65) Prior Publication Data

US 2002/0143385 A1 Oct. 3, 2002

(51) Int. Cl.⁷ .................................................. A61F 2/06
(52) U.S. Cl. ..................................................... 623/1.42
(58) Field of Search ................... 623/1.39, 1.42–1.48, 623/1.15

(56) References Cited

U.S. PATENT DOCUMENTS

| 3,657,744 A | | 4/1972 | Ersek |
| 3,988,782 A | | 11/1976 | Dardik et al. |
| 4,140,126 A | | 2/1979 | Choudhury |
| 4,755,593 A | * | 7/1988 | Lauren ....................... 530/356 |

(List continued on next page.)

FOREIGN PATENT DOCUMENTS

| EP | 0646365 | 4/1995 |
| EP | 0657147 | 6/1995 |
| EP | 0667132 | 8/1995 |
| EP | 0714269 | 6/2000 |
| WO | 9501761 | 1/1995 |
| WO | 9509586 | 4/1995 |
| WO | WO 95/10989 | 4/1995 |
| WO | 9607371 | 3/1996 |
| WO | WO 97/24081 | 7/1997 |
| WO | WO 98/25545 | 6/1998 |
| WO | 9825546 | 6/1998 |
| WO | WO 98/31305 | 7/1998 |
| WO | WO 98/34669 | 8/1998 |
| WO | WO 98/56312 | 12/1998 |
| WO | WO 99/15104 | 4/1999 |
| WO | WO 99/27989 | 6/1999 |
| WO | WO 99/38455 | 8/1999 |
| WO | WO 00/09041 | 2/2000 |
| WO | WO 00/12147 | 3/2000 |
| WO | WO 01/15633 | 3/2000 |
| WO | WO 00/18328 | 4/2000 |
| WO | WO 00/33768 | 6/2000 |
| WO | WO 00/42949 | 7/2000 |
| WO | WO 00/48530 | 8/2000 |
| WO | WO 00/49973 | 8/2000 |
| WO | WO 00/50116 | 8/2000 |
| WO | WO 01/126707 | 4/2001 |

*Primary Examiner*—David H. Willse
*Assistant Examiner*—Suzette J. Jackson
(74) *Attorney, Agent, or Firm*—Raymond Sun

(57) ABSTRACT

A prosthesis has a cylindrical stent and a cover provided about the outer periphery of the stent. The cover can be made from a water absorbent material, and a matrix of protein. The cover can be made from either tissue or hydrogel.

9 Claims, 3 Drawing Sheets

U.S. PATENT DOCUMENTS

| | | |
|---|---|---|
| 4,925,710 A | 5/1990 | Buck et al. |
| 5,122,154 A | 6/1992 | Rhodes |
| 5,123,917 A | 6/1992 | Lee |
| 5,286,254 A | 2/1994 | Shapland et al. |
| 5,383,928 A * | 1/1995 | Scott et al. ................ 623/1.15 |
| 5,389,106 A | 2/1995 | Tower |
| 5,411,550 A | 5/1995 | Herweck et al. |
| 5,466,509 A | 11/1995 | Kowligi et al. |
| 5,507,771 A | 4/1996 | Gianturco |
| 5,562,697 A | 10/1996 | Christiansen |
| 5,562,728 A | 10/1996 | Lazarus et al. |
| 5,578,075 A | 11/1996 | Dayton |
| 5,584,877 A | 12/1996 | Miyake et al. |
| 5,609,629 A | 3/1997 | Fearnot et al. |
| 5,616,608 A | 4/1997 | Kinsella et al. |
| 5,620,763 A | 4/1997 | House et al. |
| 5,628,784 A | 5/1997 | Strecker |
| 5,628,788 A | 5/1997 | Pinchuk |
| 5,637,113 A | 6/1997 | Tartaglia et al. |
| 5,674,241 A | 10/1997 | Bley et al. |
| 5,693,085 A | 12/1997 | Buirge et al. |
| 5,697,967 A | 12/1997 | Dinh et al. |
| 5,700,285 A | 12/1997 | Myers et al. |
| 5,700,286 A | 12/1997 | Tartaglia et al. |
| 5,707,385 A | 1/1998 | Williams |
| 5,709,874 A | 1/1998 | Hanson et al. |
| 5,718,973 A | 2/1998 | Lewis et al. |
| 5,723,004 A | 3/1998 | Dereume et al. |
| 5,725,567 A | 3/1998 | Wolff et al. |
| 5,733,302 A | 3/1998 | Myler et al. |
| 5,735,892 A | 4/1998 | Myers et al. |
| 5,735,897 A | 4/1998 | Buirge |
| 5,769,883 A | 6/1998 | Buscemi et al. |
| 5,779,732 A | 7/1998 | Amundson |
| 5,788,626 A | 8/1998 | Thompson |
| 5,843,166 A | 12/1998 | Lentz et al. |
| 5,857,998 A | 1/1999 | Barry |
| 5,865,723 A | 2/1999 | Love |
| 5,873,904 A | 2/1999 | Ragheb et al. |
| 5,876,432 A | 3/1999 | Lau et al. |
| 5,897,589 A | 4/1999 | Cottenceau et al. |
| 5,902,332 A | 5/1999 | Schatz |
| 5,925,074 A | 7/1999 | Gingras et al. |
| 5,925,075 A | 7/1999 | Myers et al. |
| 5,941,895 A | 8/1999 | Myler et al. |
| 5,948,018 A | 9/1999 | Dereume et al. |
| 5,951,586 A | 9/1999 | Berg et al. |
| 5,957,974 A | 9/1999 | Thompson et al. |
| 5,961,545 A | 10/1999 | Lentz et al. |
| 5,968,070 A | 10/1999 | Bley et al. |
| 5,980,565 A | 11/1999 | Jayaraman |
| 5,990,379 A | 11/1999 | Gregory |
| 6,013,099 A | 1/2000 | Dinh et al. |
| 6,117,166 A * | 9/2000 | Winston et al. ............. 623/1.13 |
| 6,139,573 A | 10/2000 | Sogard et al. |
| 6,156,064 A | 12/2000 | Chouinard |
| 6,187,039 B1 | 2/2001 | Hiles et al. |
| 6,193,746 B1 | 2/2001 | Strecker |
| 6,206,915 B1 * | 3/2001 | Fagan et al. ................ 623/1.42 |
| 6,214,039 B1 | 4/2001 | Banas et al. |
| 6,218,016 B1 | 4/2001 | Tedeschi et al. |
| 6,228,393 B1 * | 5/2001 | DiCosmo et al. ........... 424/450 |
| 6,231,605 B1 * | 5/2001 | Ku .......................... 623/11.11 |
| 6,245,099 B1 * | 6/2001 | Edwin et al. ............... 623/1.13 |
| 6,248,122 B1 | 6/2001 | Klumb et al. |
| 6,251,136 B1 * | 6/2001 | Guruwaiya et al. ......... 623/1.46 |
| 6,254,627 B1 * | 7/2001 | Freidberg ................... 623/11.11 |
| 6,355,055 B1 * | 3/2002 | Waksman et al. ........... 623/1.13 |
| 6,410,044 B1 * | 6/2002 | Chudzik et al. ............. 424/423 |
| 6,440,164 B1 * | 8/2002 | DiMatteo et al. ........... 623/1.24 |

\* cited by examiner

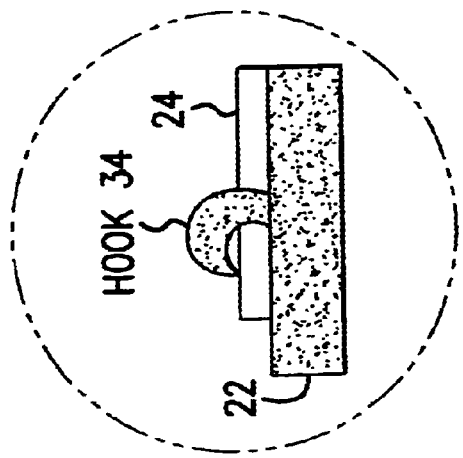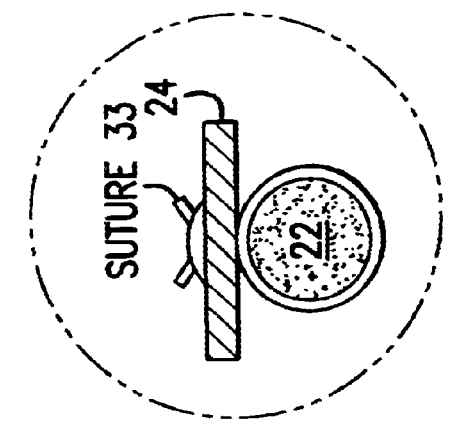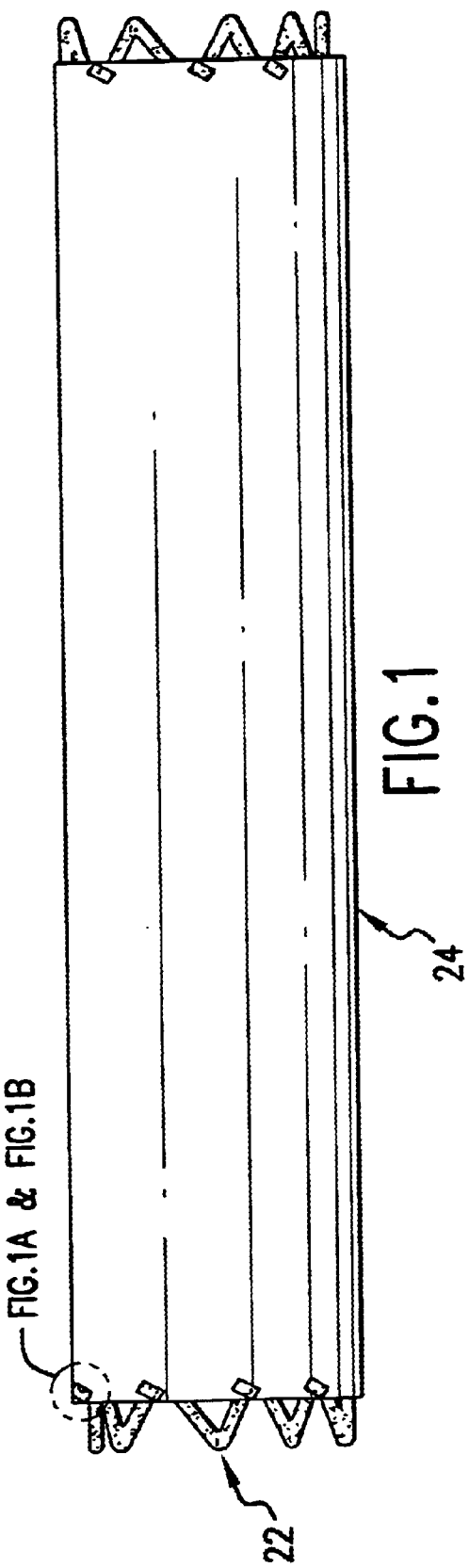

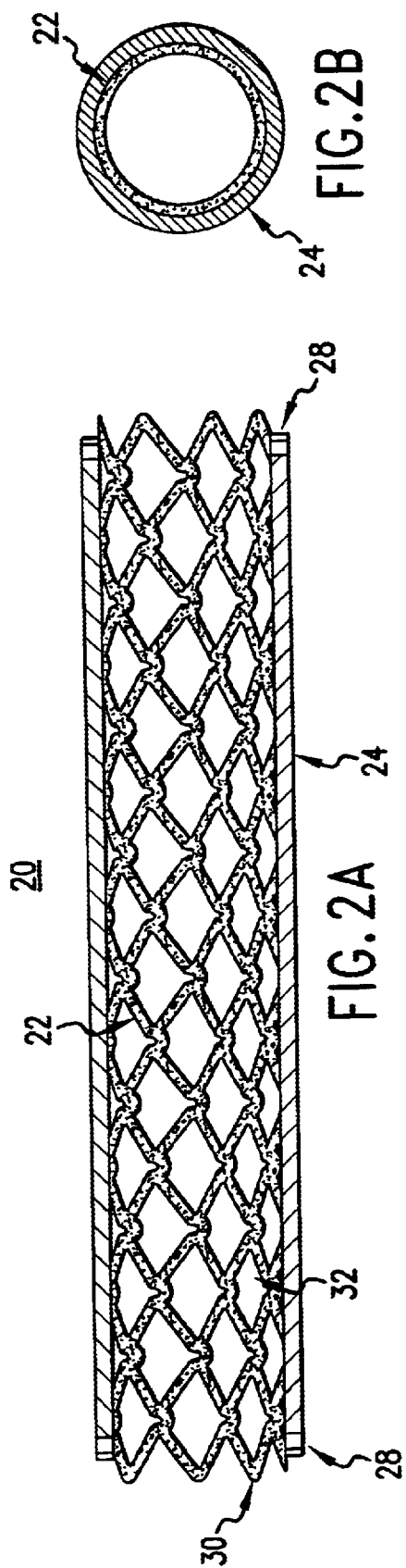

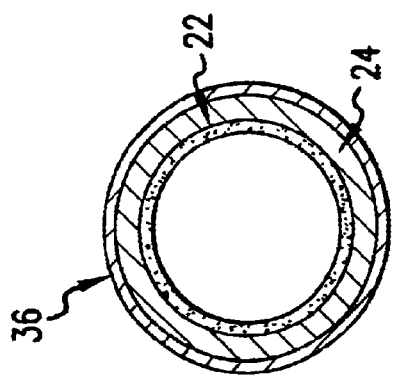
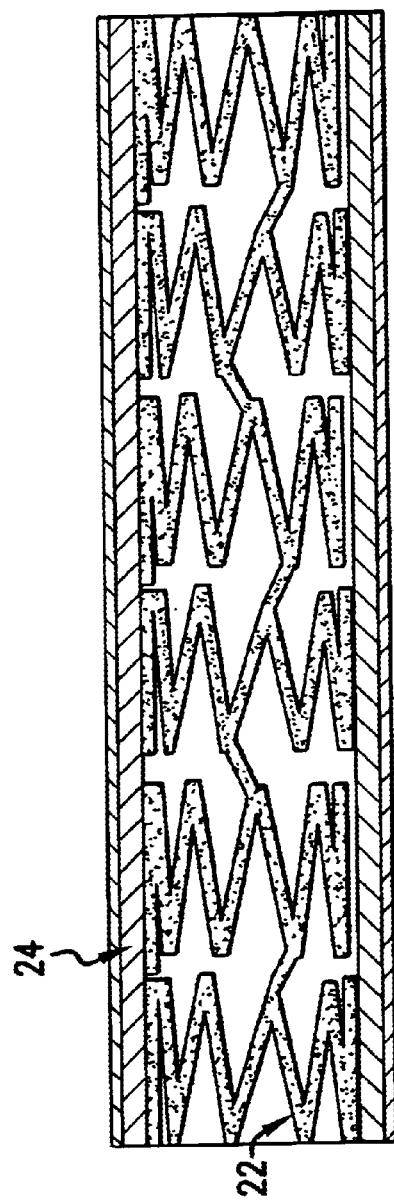

STENT HAVING COVER WITH DRUG DELIVERY CAPABILITY

BACKGROUND OF THE INVENTION

1. Field of the Invention

The present invention relates to prostheses for implantation into a mammalian vessel, and in particular, to intraluminal stents that are provided with a cover that can deliver and release drugs.

2. Description of the Prior Art

The treatment of stenosis is the subject of much research and discussion. Stenosis are currently being treated by a number of well-known procedures, including balloon dilatation, stenting, ablation, atherectomy or laser treatment.

Restenosis is the renarrowing of a peripheral or coronary artery after trauma to that artery caused by efforts to open a stenosed portion of the artery, such as by balloon dilatation, ablation, atherectomy or laser treatment of the artery. For such procedures, restenosis occurs at a rate of about 20–50% depending on the definition, vessel location, lesion length and a number of other morphological and clinical variables. Restenosis is believed to be a natural healing reaction to the injury of the arterial wall that is caused by angioplasty procedures. The host reaction begins with the thrombotic mechanism at the site of the injury. The final result of the complex steps of the healing process can be intimal hyperplasia, the uncontrolled migration and proliferation of medial smooth muscle cells, combined with their extracellular matrix production, until the artery is again stenosed or occluded.

Many attempts have been made or suggested to treat stenosis, and to prevent or minimize restenosis. One common approach is to implant intravascular stents in coronary and peripheral vessels. The stent is usually inserted by a delivery system (e.g., such as a catheter) into a vascular lumen and expanded (either via a balloon on a catheter, or through self-expansion) into contact with the diseased portion of the arterial wall to provide mechanical support for the lumen. The positioning of stent in the lumen can be used to treat stenosis by re-opening the lumen that had been partially blocked by the stenosis. However, it has been found that restenosis can still occur with such stents in place. In addition, a stent itself can cause undesirable local thrombosis. To address the problem of thrombosis, persons receiving stents also receive extensive systemic treatment with anticoagulant and antiplatelet drugs.

To address the restenosis problem, a number of approaches have been suggested. One type of approach relates to the delivery of drugs to minimize restenosis. As one example, these drugs can be delivered via oral, intravascular or intramuscular introduction, but these attempts have been largely unsuccessful. Unfortunately, pills and injections are known to be ineffective modes of administration because constant drug delivery and higher local concentration are very difficult to achieve via these means. Through repeated doses, these drugs often cycle through concentration peaks and valleys, resulting in time periods of toxicity and ineffectiveness.

Localized drug delivery is another example. There were many different attempts to provide localized drug delivery. One example of localized drug delivery is to provide the metallic walls or wires of the stents with therapeutic substances, fibrin and other drugs that can be released over a period of time at the diseased location of the vessel. However, the incorporation of drug into the walls or wires of the stent may significantly compromise the strength of the stent.

A second example of localized drug delivery is to incorporate a drug into a stent that is constructed not of metal but of a biodegradable polymer. However, the loading in and releasing of drugs from a polymeric stent may change the structural integrity and mechanical properties of the stent.

A third example of localized drug delivery is to directly coat the metal stent with a polymer that is bonded to or contains the desired drugs or anti-stenotic substances. Unfortunately, such polymer-coated stents have not been completely effective in preventing restenosis because of the cracking of the polymer as the stent is being expanded during deployment, saturation of the drug binding sites on the stent, and other reasons.

A fourth example of localized drug delivery is to provide a polymer sleeve or sheath that encompasses a portion of the stent. The sleeve or sheath would operate as a local drug delivery device. In some instances, the sheath or sleeve is made up of a bioabsorbable polymer that incorporates a drug, with the sheath or sleeve having a thickness to allow for controlled release of the drug. However, this approach suffers from the drawback that very few drugs are capable of being incorporated with common solid state polymers. In addition, directional release of drug to either the lumen or the arterial wall cannot be achieved. It will also be problematic for medical practitioners to select the type of drug and the dosage of the drug to be used, as well as the stent type to be implanted.

In addition to the problems of stenosis and restenosis, the development of cancerous blockages inside body passageways (e.g., esophagus, bile ducts, trachea, intestine, vasculature and urethra, among others) can also be treated with stents, which operate to hold open passageways which have been blocked by the cancerous growth or tumors. However, the stents do not prevent the ingrowth of the cancerous material through the interstices of the stent. If the ingrowth reaches the inside of the stent, it might result in blockage of the body passageway in which the stent had been implanted.

In addition to the above-described problems experienced by localized drug delivery, conventional stents are also ineffective in preventing the ingrowth of host tissue proliferation or inflammatory material through the interstices of the stent.

Thus, there still remains a need for a prosthesis that provides effective localized drug delivery to minimize or prevent restenosis and the ingrowth of host tissue proliferation or inflammatory material through the interstices of the stent, while avoiding the disadvantages set forth above.

SUMMARY OF THE DISCLOSURE

It is an object of the present invention to provide an intraluminal prosthesis that minimizes or prevents the ingrowth of host tissue proliferation or inflammatory material through the interstices or ends of a stent.

It is another object of the present invention to provide an intraluminal prosthesis that provides effective localized drug delivery.

In order to accomplish the objects of the present invention, there is provided a prosthesis having a cylindrical stent and a cover provided about the outer periphery of the stent. The cover can be made from a water absorbent material, and a matrix of protein. In one embodiment of the present invention, the cover is made from either tissue or hydrogel.

BRIEF DESCRIPTION OF THE DRAWINGS

FIG. 1 is a schematic view of an intraluminal prosthesis according to one embodiment of the present invention.

FIG. 1A illustrates one method of attaching the cover to the stent of the prosthesis of FIG. 1.

FIG. 1B illustrates another method of attaching the cover to the stent of the prosthesis of FIG. 1.

FIG. 2A is another schematic view of the prosthesis of FIG. 1.

FIG. 2B is a cross-sectional view of the prosthesis of FIG. 2A.

FIG. 3 illustrates yet another method of attaching the cover to the stent of the prosthesis of FIG. 1.

FIG. 4 is a cross-sectional view of the prosthesis of FIG. 3.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention provides an intraluminal prosthesis that has an underlying stent with a cover acting as a sheath or sleeve. The cover acts as a drug delivery device for locally delivering a drug to a vessel wall or lumen into which the prosthesis has been inserted and positioned. The cover also functions to block the path of cell migration (i.e., ingrowth), and to pave or act as a scaffold for supporting the lumen.

The stent according to the present invention can be any stent, including a self-expanding stent, or a stent that is radially expandable by inflating a balloon or expanded by an expansion member, or a stent that is expanded by the use of radio frequency which provides heat to cause the stent to change its size. The stent can also be made of any desired material, including a metallic material, a metal alloy (e.g., nickel-titanium) or even polymeric composites. The stent can have any wire or cell design. Examples of self-expanding wire mesh stents that can be used include the coronary Wallstent™ marketed by Schneider, and the SciMED Radius™ stent marketed by Boston Scientific Corp. Examples of balloon expandable stents that can be used include the Multilink™ stent by Guidant Corp., the Coronary Stent S670 by Medtronic AVE, the Nir™ stent by Boston Scientific Corp., the Cross Flex™ stent by Cordis, the PAS™ stent by Progressive Angioplasty Systems Inc., the V-Flex Plus™ stent by Cook, Inc., and the Palmaz-Schatz™ Crown and Spiral stents by Cordis, among others. The vessels in which the stent of the present invention can be deployed include but are not limited to natural body vessels such as ducts, arteries, trachea, veins, intestines, bile ducts, ureters and the esophagus.

The term "drug" as used herein is intended to mean any compound which has a desired pharmacologic effect. Naturally, the drug is compatible with the tissue and can be tolerated in a patient. For example, the drug can be an anticoagulant, such as an RGD peptide-containing compound, heparin, antithrombin compounds, platelet receptor antagonists, anti-thrombin antibodies, anti-platelet receptor antibodies, aspirin, protaglandin inhibitors, platelet inhibitors, or tick antiplatelet peptide. The drug can also be a promoter of vascular cell growth, such as a growth factor receptor antagonists, transcriptional activator or translational promoter. Alternatively, the drug can be an inhibitor of vascular cell growth, such as a growth factor inhibitor, growth factor receptor antagonists, transcriptional repressor or translational repressor, antisense DNA, antisense RNA, replication inhibitor, inhibitory antibodies, antibodies directed against growth factors, and bifunctional molecules. The drug can also be a cholesterol-lowering agent, a vasodilating agent, and agents which interfere with endogenous vasoactive mechanisms. Other examples of drugs can include anti-inflammatory agents, anti-platelet or fibrinolytic agents, anti-neoplastic agents, anti-allergic agents, anti-rejection agents, anti-microbial or anti-bacterial or anti-viral agents, hormones, vasoactive substances, anti-invasive factors, anti-cancer drugs, antibodies and lymphokines, anti-angiogenic agents, radioactive agents and gene therapy drugs, among others. The drug may be loaded as in its/their original commercial form, or together with polymer or protein carriers, to achieve delayed and consistent release.

Specific non-limiting examples of some drugs that fall under the above categories include paclitaxel, docetaxel and derivatives, epothilones, nitric oxide release agents, heparin, aspirin, coumadin, PPACK, hirudin, polypeptide from angiostatin and endostatin, methotrexate, 5-fluorouracil, estradiol, P-selectin Glycoprotein ligand-1 chimera, abciximab, exochelin, eleutherobin and sarcodictyin, fludarabine, sirolimus, tranilast, VEGF, transforming growth factor (TGF)-beta, Insulin-like growth factor (IGF), platelet derived growth factor (PDGF), fibroblast growth factor (FGF), RGD peptide, beta or gamma ray emitter (radioactive) agents.

The cover can be made from either a tissue or a hydrogel, as these terms are defined hereinbelow. The tissues and hydrogels according to the present invention should have a high water content and be able to absorb fluids (i.e., liquid drugs, or drugs carried in fluids).

The term "tissue" as used herein is intended to mean any mammalian (human or animal) tissue that has sufficient strength and elasticity to act as the primary component of the prosthesis. Tissue should have a cellular matrix of proteins (e.g., collagen). Tissue can include tissue that is obtained from the host patient in which the prosthesis is to be implanted (known as autologous tissue). Tissue can also include homologous tissue, such as from cadavers, umbilical cords, and placenta. In addition, tissue can include heterologous tissue, such as from swine, canine, sheep, horse, etc. Tissue can also include tissue produced in vitro using cell culture methods. In one embodiment of the present invention, luminal tissues (e.g., venous tissue such as saphenous veins, antecubital vein, cephalic vein, omental vein, mesentric vein) are preferred. The tissue can be chemically cross-linked (e.g., by glutaraldehyde, polyepoxy, PEG, UV, etc.) or not chemically cross-linked (e.g., fresh, frozen or cryopreserved). The tissue can also be chemically modified with proper charge and hydrophilicity. The tissue can be harvested according to known techniques, such as those described in Love, *Autologous Tissue Heart Valves*, R. G. Landes Co., Austin, Tex., 1993, Chapter 8.

The term "hydrogel" as used herein is intended to mean a natural gel-like material that is formed by protein. The hydrogel material has a proper hydrophilicity to regulate the water and drug diffusion process. The release of the drugs is accomplished by other charged particles in the patient's body which competes with the charged binding site in the hydrogel material for the drug. Hydrogel can include albumin, collagen, gelatin, starch, celluloses, dextran, polymalic acid, polyamino acids and their co-polymers or lightly cross-linked forms. Other possible materials are polysaccharides and their derivatives. Yet other possible materials include sodium alginate, karaya gum, gelatin, guar gum, agar, algin, carrageenans, pectin, locust bean gums, xanthan, starch-based gums, hydroxyalkyl and ethyl ethers of cellulose, sodium carboxymethylcellulose. Some are food gels and some are bioadhesives.

The term "material" as used herein means either tissue or hydrogel.

FIGS. 1, 2A and 2B illustrate a prosthesis 20 according to one embodiment of the present invention. The prosthesis 20 has a tubular stent 22 and a cover 24 attached over the outer periphery of the stent 22. As described above, the stent 22 can be any known or conventional stent, and as a non-limiting example, FIG. 2A illustrates the stent 22 as being a self-expanding Nir™ stent by Boston Scientific Corp., as described in FIG. 8 of U.S. Pat. No. 5,733,303 to Israel et al., whose disclosure is incorporated herein as though fully set forth herein.

The cover 24 acts as a drug reservoir that stores the drug(s) to be released at the site of implantation of the prosthesis 20. The cover 24 is extensible (i.e., can be stretched) and flexible, and has the ability to absorb drugs and to store the drug(s) before the prosthesis 20 is deployed. The cover 24 can be either a single-layer of material (such as tissue or hydrogel) or multiple layers of material. When multiple layers are used, the layers can include (1) tissue with hydrogel layer, (2) polymer (non-drug loading) layer with hydrogel layer, (3) polymer (non-drug loading) layer with cultured tissue layer (e.g., culture collagen, elastin, crosslinked soluble protein, etc.), (4) hydrogel layer with hydrogel layer (e.g., two hydrogel layers having different drug release rates), and (5) polymer (non-drug loading) layer with tissue layer, among others. In the multiple-layer configuration, at least one material layer will absorb the drug, and one of the layers can be a non-drug loading layer. The non-drug loading layer would not contain any drug(s), and may be made of nonhydrogel polymers, such as polyurethanes, expanded PTFE, polyesters, polyamides, polylactide, polylactide-co-glycolide, polydioxanone, thermoplastic elastomers, thermoplastics, and silicone rubbers. The non-drug loading layer facilitates directional drug delivery since this layer forms a barrier against drug diffusion.

In the embodiment of FIGS. 1–2B, there are a number of ways of loading the drug(s) to the cover 24. The material utilized for the cover 24 may have water content greater than 90% by weight. If so, the water can be removed by a lyophilization process that is a well-known technique in the art.

One method involves physical absorption into the cover 24. Under this method, the drug is loaded into the material during the rehydration process. The drug may be dissolved in a physiological solution for rehydration of the lyophilized material. If the drug has limited solubility in water, additional solvent may be added to facilitate the dissolving process, as long as the solvent has no adverse effects on the cover and the host patient. As an example, ethanol at a concentration of less than 50% v/v may be suitable for the rehydration process. The rehydration process for tissue and hydrogel is fast, easy and complete. The material has no noticeable change in property before dehydration and after complete rehydration. By changing the hydrophilicity of the material, the drug may be released at different rates.

A second method involves the use of a charged chemical to electronically attract and retain drugs. In particular, natural tissue and the hydrogels defined above are proteins, which are composed of amino acids with various kinds of functional groups. By choosing the appropriate modification reagent, it is possible to selectively reduce certain groups to imbalance the surface and matrix charge of the tissue or hydrogel to either positive or negative. For example, aldehyde group will react with amino group to change the surface and matrix charge to negative. Carbodiimide reaction will target the free carboxyl group to change the surface and matrix charge to positive. Addition of charged chemicals into tissue may also change the net electricity of the tissue. A charged tissue or hydrogel material has the tendency to electronically attract and retain a drug carrying the opposite charge. The drug will then be released inside the vessel after implantation. The release of the drugs is accomplished by other charged particles in the patient's body which competes with the charged binding site in the hydrogel material for the drug.

A third method involves chemical reaction or bonding to link certain drugs to the material. The bonding may be covalent or ionic. For example, heparin may be immobilized to tissue surface covalently through direct Carbodiimide reaction or with polyethylene oxide as a bridge or spacer. Heparin can also link to tissue through ionic interaction through benzalkonium or stearylkonium. The drug may be released or remain on the surface of the tissue or hydrogel with activity in the vessel.

A fourth method involves coating the surface of the tissue or hydrogel. For example, the drug can be sprayed onto the surface, and then a gel-like material may be used to coat the tissue or hydrogel. As another example, it is also possible to first mix the gel with the drug, and then coat the mixture on to the material. As yet another example, the gel may be applied over the outer layer of the tissue or hydrogel before the drug is loaded. Then, just before implantation, the cover 24 can be immersed in a solution containing the drug, and the nature of the gel will cause the drug to be retained or loaded in the gel. The prosthesis 20 can then be delivered inside the desired vessel and the drug will be released over a period of time. Examples of the gel-like material can include polyethylene oxide, polyvinyl pyrrolidone, polyacrylates, and their blends or co-polymers or lightly crosslinked forms. Other examples include polyethylene glycol block copolymers with polylactides or other polyesters. Yet other examples include hydrophilic polyurethane, poly(maleic andydride-alt-ethylene) and their derivatives. Further examples include polysaccharides and their derivatives, sodium alginate, karaya gum, gelatin, guar gum, agar, algin, carrageenans, pectin, locust bean gums, xanthan, starch-based gums, hydroxyalkyl and ethyl ethers of cellulose, sodium carboxymethylcellulose. Some of these gel-like materials can be heated and then cooled to form the gel. Some are food gels and some are bioadhesives.

The cover 24 can be attached to the stent 22 by suturing the ends 28 of the cover 24 to the desired portions of the stent 22. For example, the cover 24 can be the same length as the stent 22, in which the ends 28 of the cover 24 are sutured (e.g., see suture 33 in FIG. 1A) to the ends 30 of the stent 22. If the length of the cover 24 is less than the length of the stent 22, then the ends 28 of the cover 24 can be sutured to selected wires (e.g., 32) of the stent 22 so that the cover 24 covers a portion of the stent 22. Other methods of attachment include the use of hooks or barbed mechanisms 34 on the stent 22 to hook the cover 24 to the stent 22 (see FIG. 1B), or the use of glue to attach selected portions of the cover 24 to selected portions of the stent 22. Another method of attachment can include the use of an overlaying or wrapping membrane 36 that covers the cover 24 and the stent 22, but which is removable with the delivery catheter after the prosthesis 20 has been delivered to the desired location in the vessel.

The cover 24 can be provided in the form of a tubular cover (i.e., luminal) or as a sheet that can be formed into a tubular cover by suturing or stitching side edges of the sheet. If the cover 24 is luminal, the cover 24 can be slid over the stent 22 and then attached. If the cover 24 is provided in the form of a sheet of material, the sheet of material can be merely wrapped around the stent 22, and no stitching is required. In either case, the attachment can done with the stent 22 in the expanded state or in the compressed state. If the attachment is done in the expanded state, the prosthesis 20 is then compressed to a smaller diameter for delivery. When the prosthesis 20 is compressed, the flexible and stretchable nature of the cover 24 would allow the cover 24 to compress with the stent 22 without any creasing. Similarly, if the attachment is done in the compressed state, the flexible and stretchable nature of the cover 24 would allow the cover 24 to expand (e.g., stretch) with the expanding stent 22 when the prosthesis 20 is expanded.

The prosthesis 20 can be implanted using any known methods for the underlying stent 22. A catheter can be used to deliver the prosthesis 20 to the desired location in the vessel, and then the stent 22 can be expanded (i.e., either self-expanding or balloon expanded, depending on the type of stent). In essence, the prosthesis 20 will be deployed and used in the same manner as its underlying stent 22. The deployment techniques and functions of the stent 22 are well-known, and shall not be explained in greater detail.

The drug contained in the cover 24 can be released by diffusion, or by any of the methods described above. Since tissue and hydrogel are water permeable, water and molecules can diffuse through the tissue or hydrogel cover 24 at different rates. The A idiffusion rate can be controlled by varying the thickness of the cover 24, changing the size of the migrating molecules (either the drug alone or with a carrier to form a larger molecule to slow down the diffusion process), changing the hydrophilicity of the cover 24, changing the drug concentration (i.e., drug released from its polymeric carrier), and coating the surface of the cover 24 with polymeric material having different permeability.

Thus, the cover 24 of the present invention provides a sheath or sleeve to block the path of cell migration (i.e., ingrowth), and to pave or act as a scaffold for supporting the lumen. The cover 24 acts as an effective drug delivery device for locally delivering a drug to an arterial wall or lumen into which the prosthesis 20 has been inserted and positioned.

EXAMPLE 1

A dried tissue stent cover made of polyepoxy crosslinked porcine venous tissue, 25 μm thick at its collapsed diameter and 30 μm long (0.5 mg dried weight), is soaked in approximately 5 mg of water or any liquid medication during its rehydration process.

EXAMPLE 2

A polymeric stent cover, made of ePTFE, is provided with another layer of Taxol, gelatin, and poly(e-caprolactone) mixture (20:20:60) on the outside. 20% of the Taxol is released to the artery wall during the first week after implantation.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A prosthesis, comprising:
   a cylindrical stent having an outer periphery; and
   a cover provided about the outer periphery of the stent, the cover made of a natural tissue that has been chemically modified, and which has a drug incorporated therein;
   wherein the cover is charged for drug absorption.

2. The prosthesis of claim 1, wherein the cover is made up of a matrix of protein.

3. The prosthesis of claim 1, wherein the cover is stitched to the stent.

4. The prosthesis of claim 1, wherein the cover comprises two layers of material.

5. The prosthesis of claim 4, wherein one of the layers of materials is a non-drug loading layer.

6. A cover, comprising:
   a cylindrical stent having an outer periphery; and
   a cover provided about the outer periphery of the stent, the cover made of a natural tissue that has been chemically modified, and which has a drug incorporated therein;
   p1 wherein the cover is charged for drug absorption.

7. The cover of claim 6, wherein the cover is made up of a matrix of protein.

8. The cover of claim 7, wherein the cover comprises two layers of material.

9. The prosthesis of claim 8, wherein one of the layers of materials is a non-drug loading layer.

* * * * *